(12) United States Patent
Tsuru et al.

(10) Patent No.: US 10,940,121 B2
(45) Date of Patent: *Mar. 9, 2021

(54) GEL PATCH

(71) Applicant: HISAMITSU PHARMACEUTICAL CO., INC., Tosu-shi, Saga (JP)

(72) Inventors: Seiichiro Tsuru, Tosu (JP); Masayoshi Maki, Tosu (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/551,916

(22) PCT Filed: Feb. 17, 2016

(86) PCT No.: PCT/JP2016/054570
§ 371 (c)(1),
(2) Date: Aug. 18, 2017

(87) PCT Pub. No.: WO2016/136556
PCT Pub. Date: Sep. 1, 2016

(65) Prior Publication Data
US 2018/0036255 A1 Feb. 8, 2018

(30) Foreign Application Priority Data

Feb. 24, 2015 (JP) .............................. JP2015-033981
Apr. 10, 2015 (JP) .............................. JP2015-080888

(51) Int. Cl.
| | | |
|---|---|---|
| A61K 9/70 | (2006.01) | |
| A61K 47/10 | (2017.01) | |
| A61K 47/32 | (2006.01) | |
| A61K 31/196 | (2006.01) | |
| A61K 45/00 | (2006.01) | |
| A61K 31/192 | (2006.01) | |

(52) U.S. Cl.
CPC .............. *A61K 9/7038* (2013.01); *A61K 9/70* (2013.01); *A61K 31/192* (2013.01); *A61K 45/00* (2013.01); *A61K 47/10* (2013.01); *A61K 47/32* (2013.01)

(58) Field of Classification Search
None
See application file for complete search history.

(56) References Cited

U.S. PATENT DOCUMENTS

| | | | | |
|---|---|---|---|---|
| 5,232,702 | A * | 8/1993 | Pfister .................. | A61K 9/7069 424/448 |
| 6,239,177 | B1 | 5/2001 | Mori et al. | |
| 6,914,169 | B1 * | 7/2005 | Oota .................... | A61K 9/7053 602/43 |
| 2009/0043236 | A1 | 2/2009 | Kawamura et al. | |
| 2012/0102242 | A1 | 4/2012 | Koren et al. | |
| 2014/0302118 | A1 | 10/2014 | Kawamura et al. | |
| 2016/0175262 | A1 * | 6/2016 | Tsurushima ........... | A61K 47/14 424/402 |
| 2016/0206569 | A1 * | 7/2016 | Tsurushima ........... | A61K 9/7061 |
| 2017/0348248 | A1 * | 12/2017 | Tsurushima ........... | A61K 9/7061 |

FOREIGN PATENT DOCUMENTS

| | | |
|---|---|---|
| CN | 101184479 A | 5/2008 |
| CN | 103313710 A | 9/2013 |
| JP | S60-4125 A | 1/1985 |
| JP | 2837337 B2 | 12/1998 |
| JP | H11-12910 A | 1/1999 |
| JP | H11-188054 A | 7/1999 |
| JP | 2000143503 A | 5/2000 |
| JP | 2001-302503 A | 10/2001 |
| JP | 2003-155252 A | 5/2003 |
| JP | 2007-39451 A | 2/2007 |
| JP | 2007-269712 A | 10/2007 |
| JP | 2007-320939 A | 12/2007 |
| JP | 2008037798 A * | 2/2008 |
| JP | 2008037798 A | 2/2008 |
| JP | WO2012102242 A1 | 8/2012 |
| JP | 2013-82650 A | 5/2013 |
| KR | 1020010111593 A | 12/2001 |
| KR | 1020080015120 A | 2/2008 |
| WO | 9728793 A1 | 8/1997 |
| WO | 0183866 A2 | 11/2001 |
| WO | 2006/070672 A1 | 7/2006 |
| WO | 2006/090782 A1 | 8/2006 |
| WO | 2006/129745 A1 | 12/2006 |
| WO | 2010073327 A1 | 7/2010 |
| WO | WO-2012102242 A1 * | 8/2012 ........... A61K 9/7038 |
| WO | 2013/027840 A1 | 2/2013 |

OTHER PUBLICATIONS

Cilurzo et al., Expert Opin. Drug Deliv., 9(1), pp. 33-45. (Year: 2012).*
Wang et al., Rheological Characterization of Cataplasm Bases Composed of Cross-linked Partially Neutralized Polyacrylate Hydrogel, AAPS PharmSciTech, 15(5), pp. 1149-1154. (Year: 2014).*
International Search Report dated Mar. 15, 2016 issued in corresponding International Application No. PCT/JP2016/054570.
International Preliminary Report on Patent ability dated Sep. 8, 2017 in corresponding counterpart International Patent Application No. PCT/JP2016/054570.
Extended European search report dated Jul. 18, 2018 for corresponding application No. 16755303.1.
JSL (Japaneses Industrial Standard) L 1018, 1999, pp. 819, 822, and 826.

(Continued)

*Primary Examiner* — Abigail Vanhorn
(74) *Attorney, Agent, or Firm* — Nath, Goldberg & Meyer; Joshua B. Goldberg (57) ABSTRACT

A method for producing a gel patch comprising an adhesive mass layer on a backing fabric, comprising a step of applying a composition comprising a physiologically active substance, a water-soluble polymer, glycerin, and water to the backing fabric to form the adhesive mass layer, wherein a loss tangent of the composition in dynamic viscoelasticity measurement at 1 Hz at a time of application to the backing fabric is 0.75 to 1.

5 Claims, 2 Drawing Sheets

(56) References Cited

OTHER PUBLICATIONS

Meng, Shengnan, "Pharmacology", Sep. 2011, p. 158.
Zhang, Yuan, "Chinese medicine formulation technology", Aug. 2012, p. 262-p. 263, p. 280.
Japanese Office Action dated Apr. 14, 2020 corresponding to application No. 2016-566128.
Chinese Office Action dated May 29, 2020 corresponding to application No. 201680004916.1.
Office Action dated Oct. 13, 2020 corresponding to BR Patent Application No. BR1120170172879.

* cited by examiner

GEL PATCH

This is a National Phase Application filed under 35 U.S.C. 371 as a national stage of PCT/JP2016/054570, filed Feb. 17, 2016, an application claiming the benefit of Japanese Application No. 2015-033981, filed Feb. 24, 2015 and Japanese Application No. 2015-080888, filed Apr. 10, 2015, the content of each of which is hereby incorporated by reference in its entirety.

TECHNICAL FIELD

The present invention relates to a gel patch.

BACKGROUND ART

Gel patch are one type of transdermal patches produced by applying a medicament-containing adhesive mass layer on a backing fabric, and generally, contains a large amount of moisture and the adhesive mass layer is thick. Since the gel patch has such a configuration, the penetration of active ingredients into the skin is promoted to reduce skin irritation.

In the gel patch, components of the adhesive mass layer greatly contribute to the performance of the patch, such as tack strength. In order to increase the tackiness or skin adhesion of the patch, adjustment of a dynamic viscoelasticity measurement value is investigated in Patent Literatures 1 and 2. On the other hand, a tape is investigated in which a pressure-sensitive adhesive layer that does not comprise water is laminated on a backing fabric such as a knitted fabric, and such a tape has good conformability to the skin and also good adhesion.

CITATION LIST

Patent Literature

Patent Literature 1: WO 2006/129745 A
Patent Literature 2: JP S60-4125 A
Patent Literature 3: JP H11-188054 A

SUMMARY OF INVENTION

Technical Problem

According to the findings of the inventors, when a backing fabric such as a knitted fabric is laminated on the adhesive mass layer of a gel patch, components of the adhesive mass layer may ooze out to the back side of the backing fabric (the surface on the side opposite the surface in contact with the adhesive mass layer) even if the adhesive mass layer comprises a large amount of water.

Accordingly, an objective of the present invention is to provide a method for producing a gel patch in which, even when a backing fabric such as a knitted fabric is laminated on an adhesive mass layer comprising a large amount of water, components of the adhesive mass layer are unlikely to ooze out to the back side of the backing fabric.

Solution to Problem

The present invention provides a method for producing a gel patch comprising an adhesive mass layer on a backing fabric, comprising a step of applying a composition comprising a physiologically active substance, a water-soluble polymer, glycerin, and water to the backing fabric to form the adhesive mass layer, wherein a loss tangent of the composition in dynamic viscoelasticity measurement at 1 Hz at a time of application to the backing fabric is 0.75 to 1.

Thus, by setting the loss tangent at the time of application to the backing fabric of the composition comprising the above components within the numerical range described above, even when the backing fabric such as a knitted fabric is laminated on the adhesive mass layer comprising a large amount of water, the components of the adhesive mass layer are unlikely to ooze out to the back side of the backing fabric during the production of the gel patch.

In the present invention, it is preferable that the backing fabric is a knitted fabric, and the elongation recovery ratio of the knitted fabric is 73 to 98% in the course direction, and 83 to 98% in the wale direction. Moreover, it is preferable that the backing fabric is a knitted fabric, and the bending resistance of the knitted fabric is 10 to 15 mm in the course direction and 10 to 18 mm in the wale direction.

By using a backing fabric having an elongation recovery ratio and/or a bending resistance as described above as a backing fabric to which the composition is applied, components of the adhesive mass layer are more securely prevented from oozing out when the adhesive mass layer consisting of the composition having a loss tangent of 035 to 1 in dynamic viscoelasticity measurement at 1 Hz at the time of application is formed on the backing fabric.

Moreover, adopting the production method as described above makes it possible to comprise a methyl acrylate/2-ethylhexyl acrylate copolymer resin (also referred to as poly(methyl acrylate/2-ethylhexyl acrylate). That is to say, the adhesive mass layer is prevented from oozing out to the back side of the backing fabric even if an emulsion of a methyl acrylate/2-ethylhexyl acrylate copolymer resin or the like is included thereto.

It is preferable that the content of the water-soluble polymer is 3 to 18% by mass based on the mass of the whole adhesive mass layer. Regulating the content of the water-soluble polymer to such a range makes it possible to increase the performance of the gel patch and prevent the adhesive mass layer from oozing out to the back side of the backing fabric.

A gel patch is obtained by the above production method. In this gel patch, the adhesive mass layer is prevented from oozing out to the back side of the backing fabric, therefore uniform tackiness can be obtained, and the percutaneous absorption of the physiologically active substance is also secured. Moreover, disadvantages due to the adhesive mass layer that has oozed out to the back side of the backing fabric, such as making the hand sticky during attachment, and making the patch adhered to the inside of a packaging during storage, are overcome.

Advantageous Effects of Invention

According to the method for producing a gel patch of the present invention, even when a backing fabric such as a knitted fabric is laminated on an adhesive mass layer comprising a large amount of water, components of the adhesive mass layer are unlikely to ooze out to the back side of the backing fabric.

DESCRIPTION OF EMBODIMENTS

Below, one embodiment is provided to describe the present invention.

In this specification, the loss tangent (tan δ) value calculated by the following formula in dynamic viscoelasticity measurement where a composition comprising a physiologically active substance, a water-soluble polymer, glycerin, and water is sandwiched between two plates, and a change of stress when periodically vibrating distortion is applied to one plate is measured. Dynamic viscoelasticity measurement is performed, for example, at a temperature of 32° C. at a frequency of 1 Hz using a rotary rheometer.

Loss tangent (tan δ)=Loss modulus (G")/Storage modulus (G')

The method for producing a gel patch according to the present embodiment comprises the step of applying a composition (hereinafter sometimes referred to as an "adhesive mass fluid" for convenience) comprising a physiologically active substance, a water-soluble polymer, glycerin, and water to the backing fabric to form an adhesive mass layer.

First, the backing fabric, and the composition for forming the adhesive mass layer, used in the method for producing a gel patch according the present embodiment will now be described.

Examples of the backing fabric include a woven fabric, a non-woven fabric, a resin film, a foamed sheet, and paper, and the woven fabric is, for example, a knitted fabric. When a woven fabric, a non-woven fabric, or a resin film is used as the backing fabric, examples of components thereof include polyolefins such as polyethylene, polypropylene, and polybutylene, polyesters such as polyethylene terephthalate, rayon, polyurethane, and cotton. One of these may be used alone, or two or more may be used in combination. The backing fabric may have a single-layer structure, or may have a multilayer structure. It is more preferable that the material of the backing fabric is polyester.

It is preferable that the backing fabric is a knitted fabric or a non-woven fabric. The knitted fabric is roughly divided into a weft-knitted fabric and a warp-knitted fabric, and examples of the warp-knitted fabric include those obtained by plain stitch (stockinette stitch, jersey stitch), rib stitch (ribbing), purl stitch (garter stitch), and smooth stitch (interlock stitch). Examples of the weft-knitted fabric include those obtained by Denbigh stitch, Vandyke stitch, cord stitch, atlas stitch, and multiaxial inlay stitch. While any such knitted fabrics are suitably used, a knitted fabric by plain stitch is particularly preferable.

When the backing fabric is a knitted fabric or a non-woven fabric, it is preferable that the amount is 80 to 150 g/m$^2$, and more preferably 95 to 125 g/m$^2$ because spreading a water-containing adhesive mass onto a woven fabric possibly causes the adhesive mass to ooze out to the back side of the backing fabric through the meshes of the woven fabric. By regulating the amount to such a range, there is a tendency that the adhesive mass can be spread without allowing it to ooze out to the back side of the backing fabric through the gaps in the backing fabric, and it is possible to maintain anchoring properties between the backing fabric and the adhesive mass.

A preferable example of the knitted fabric is a knitted fabric obtained from one polyester, nylon, polypropylene, or rayon material, or two or more in combination, and in particular a knitted fabric consisting of polyethylene terephthalate, which is a polyester material and whose interaction with a medicament is small, is more preferable.

When a knitted fabric is used as the backing fabric, a knitted fabric having a predetermined elongation recovery ratio is particularly preferable. Here, the elongation recovery ratio is a value measured in accordance with "JIS L 1096: 2010 Testing methods for woven and knitted fabrics". The use of a knitted fabric having a predetermined elongation recovery ratio is preferable because when the gel patch is affixed to a moving part such as a joint, the backing fabric expands or contracts in accordance with the movement of the affixed site.

Figure 1:
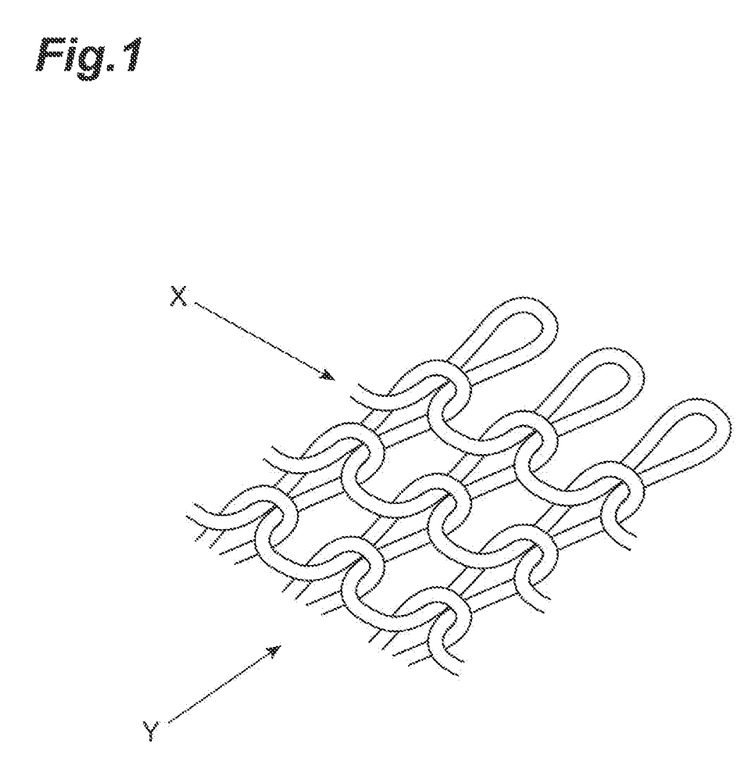
FIG. 1 is a perspective view showing the course direction and the wale direction in a weft-knitted fabric.
Figure 2:
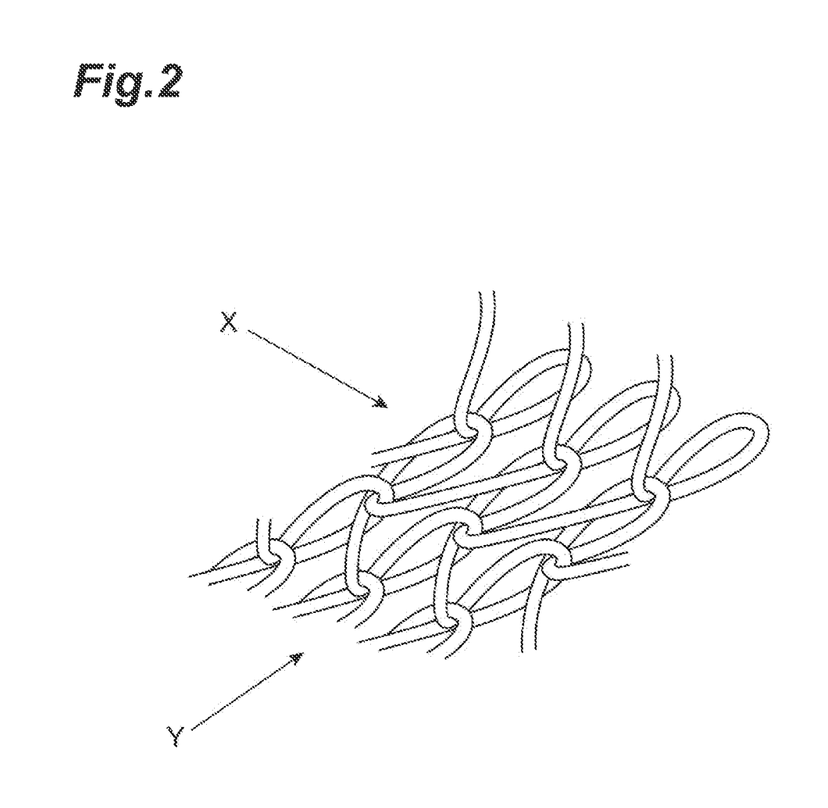
FIG. 2 is a perspective view showing the course direction and the wale direction in a warp-knitted fabric.

When the backing fabric is a knitted fabric, it is preferable that the 50% elongation recovery ratio of the knitted fabric is 73 to 98% in the course direction and 83 to 98% in the wale direction, and more preferably 75 to 97% in the course direction and 85 to 97% in the wale direction. The course direction and the wale direction in a knitted fabric will now be described using FIGS. 1 and 2. FIG. 1 is a perspective view showing the course direction and the wale direction in a weft-knitted fabric. FIG. 2 is a perspective view showing the course direction and the wale direction in a warp-knitted fabric. The direction indicated by X in FIGS. 1 and 2 is the course direction, and means the weft direction of the knitted fabric. The direction indicated by Y in FIGS. 1 and 2 is the wale direction, and means the warp direction of the knitted fabric.

It is preferable that the bending resistance of the backing fabric is 10 to 15 mm in the course direction and 10 to 18 mm in the wale direction, and more preferably 10 to 13 mm in the course direction and 10 to 15 mm in the wale direction. The method for measuring bending resistance is in accordance with JIS L 1096:2010, 45° Cantilever method.

It is preferable for the knitted fabric that the 50% modulus (load at 50% elongation) is 2 to 12 N/5 cm in the course direction, and the 50% modulus is 2 to 12 N/5 cm in the wale direction, and more preferable that the 50% modulus is 2 to 8 N/5 cm in the course direction and 2 to 12 N/5 cm in the wale direction. The method for measuring the modulus is in accordance with JIS L 1018:1999. When the 50% modulus is lower than 2 N/5 cm in the course direction or the wale direction, there is a possibility that the knitted fabric stretches when the adhesive mass is applied, and the pressure-sensitive adhesive oozes into the mesh. When the 50% modulus of the knitted fabric is higher than 8 N/5 cm in the course direction or 12 N/5 cm in the wale direction, stretchability is inferior, and the knitted fabric may be unlikely to conform to the stretching of the skin when the knitted fabric is applied to a flection part.

When a thick backing fabric having a thickness of about 0.55 to 0.8 mm is used, there is a tendency that the components contained in the adhesive mass layer can be more suppressed from oozing out to the back side of the backing fabric. When a thin backing fabric having a thickness of about 0.4 to 0.65 mm is used, the level difference relative to the skin when attached is small, and the gel patch is less likely to peel off from the skin during the use thereof, and influences thereof on daily activities such as dressing and undressing are also small.

The adhesive mass fluid (the composition for forming the adhesive mass layer) comprises a physiologically active substance, a water-soluble polymer, glycerin, and water.

The physiologically active substance has percutaneous absorbability and exhibits in vivo pharmacological activity, and examples include non-steroidal anti-inflammatory agents such as felbinac, flurbiprofen, diclofenac, diclofenac sodium, methyl salicylate, glycol salicylate, indomethacin, ketoprofen, and ibuprofen, or esters thereof; antihistamines such as diphenhydramine and chlorpheniramine; analgesics such as aspirin, acetaminophen, ibuprofen, and loxoprofen sodium; locally acting anesthetics such as lidocaine and dibucaine; muscle relaxants such as suxamethonium chloride; antifungal agents such as clotrimazole; antihypertensives such as clonidine; vasodilators such as nitroglycerin and isosorbide nitrate; vitamins such as vitamin A, vitamin E (tocopherol), tocopherol acetate, vitamin K, octotiamine, and riboflavin butyrate; and prostaglandins, scopolamine, fentanyl, 1-menthol, *capsicum* extract, and N-vanillyl nonamide.

The adhesive mass fluid comprises a water-soluble polymer, and this water-soluble polymer means a macromolecule having a hydrophilic group. Examples of the hydrophilic group include a hydroxy group, a carboxy group, and an amino group. Due to the water-soluble polymer contained, water in the gel patch can be retained for a longer period of time.

It is preferable that a polyacrylic acid or a neutralized polyacrylate (these may be referred to as "water-soluble acrylic polymers") is contained as a water-soluble polymer. Due to the polyacrylic acid or the neutralized product thereof contained in an adhesive mass layer, a gel patch having an adhesive mass layer with better adhesion can be obtained.

The water-soluble acrylic polymer is a polymer obtained by polymerizing an acryloyl group-containing compound having a functional group (a hydrophilic group) that exerts water solubility, and exerts adhesion by being contained in the adhesive mass layer together with water. The water-soluble acrylic polymer is a polymer obtained by, for example, polymerizing a compound having an acryloyl group, such as a polyacrylic acid or neutralized product thereof, an acrylic acid ester having a hydrophilic group, or an acrylic acid amide having a hydrophilic group. The water-soluble acrylic polymer may be a homopolymer obtained from one compound having an acryloyl group, or may be a copolymer obtained from two or more compounds having acryloyl groups.

The hydrophilic group may be any of the cationic hydrophilic group, anionic hydrophilic group, and nonionic hydrophilic group. Examples of the cationic hydrophilic group include a quaternary ammonium group, examples of the anionic hydrophilic group include a carboxy group, a sulfo group, and a phosphate group, and examples of the nonionic hydrophilic group include a hydroxy group and an amino group.

When a polyacrylic acid is contained as a water-soluble polymer, it is preferable to regulate the content thereof to 1 to 5% by mass and more preferable to regulate it to 2 to 6% by mass based on the mass of the whole adhesive mass layer. With the content of the water-soluble polymer being 1% by mass or more, there is a tendency that the moldability and shape retainability of the adhesive mass layer are more improved, and with the content of the polyacrylic acid being 5% by mass or less, there is a tendency that the hardness of the adhesive mass layer is unlikely to be high, adhesion to the skin is more increased.

The neutralized polyacrylate may be a completely-neutralized polyacrylate, may be a partially-neutralized polyacrylate, or may be a mixture of these. An example of the neutralized polyacrylate is a polyacrylic acid salt and, for example, a sodium salt, a potassium salt, a calcium salt, and an ammonium salt can be used.

It is preferable that the neutralized polyacrylate is a partially-neutralized polyacrylate because the initial adhesion strength and the over-time adhesion strength are high. The partially-neutralized polyacrylate has a structural unit derived from acrylic acid and a structural unit derived from an acrylic acid salt in any proportion in one polymer chain. It is preferable to use a partially-neutralized polyacrylate in which 20 to 80 mol % of the carboxy groups in one polymer chain are neutralized.

When a neutralized polyacrylate is contained as a water-soluble polymer, it is preferable to regulate the content thereof to 1 to 6% by mass, and more preferable to regulate it to 2 to 6% by mass, based on the mass of the whole adhesive mass layer. With the content of the neutralized polyacrylate being 1% by mass or more, the adhesion strength of the neutralized polyacrylate is sufficiently obtained, and with the content of the neutralized polyacrylate being 6% by mass or less, the moldability and the shape retainability of the adhesive mass layer are improved. When a polyacrylic acid and a neutralized polyacrylate (preferably a partially-neutralized polyacrylate) are used in combination as a water-soluble polymer, the respective suitable contents thereof are also as those described above.

In the acrylic acid ester having a hydrophilic group, the acrylic acid ester portion is preferably an alkyl acrylate. It is preferable that the alkyl portion thereof is an alkyl having 1 to 10 carbon atoms, and more preferably an alkyl having 1 to 8 carbon atoms. In the acrylic ester having a hydrophilic group, it is preferable that the hydrophilic group is present in this alkyl moiety.

Other than the water-soluble acrylic polymer, the water-soluble polymer may contain, for example, gelatin, polyvinyl alcohol, polyvinylpyrrolidone, sodium alginate, hydroxypropylcellulose, sodium carboxymethylcellulose (carmellose sodium), methylcellulose, carrageenan, glucomannan, agar, guar gum, xanthan gum, gellan gum, pectin, or locust bean gum. One of these may be used singly, or two or more may be used in combination. It is preferable that the water-soluble polymer is carmellose sodium, gelatin, or polyvinyl alcohol. These may be used in combination with the water-soluble acrylic polymer.

When a water-soluble polymer other than the water-soluble acrylic polymer is contained as the water-soluble polymer, it is preferable to regulate the content thereof to 3 to 18% by mass, and more preferable to regulate it to 3 to 10% by mass, based on the mass of the whole adhesive mass layer. With the content of the water-soluble polymer being 3% by mass or more, there is a tendency that the cohesive strength of the adhesive mass layer is likely to be high, and with 10% by mass or less, there is a tendency that the contained physiologically active substance is likely to be uniformly dispersed in the adhesive mass layer.

It is preferable to regulate the content of glycerin to 5 to 50 mass, more preferable to regulate it to 7 to 25% by mass, and even more preferably 10 to 20% by mass, based on the mass of the whole adhesive mass layer.

Due to the contained glycerin, there is a tendency that the adhesive mass layer is softer, and the adhesion of the gel patch is more improved. When the content of glycerin is 5% by mass or more, drying of the adhesive mass layer can be more retarded during the use of the gel patch, thus making it easy to maintain the adhesion strength of the gel patch for a long period of time. Also, when the content of glycerin is 50% by mass or less, glycerin is unlikely to be dissociated from the adhesive mass layer, and the surface of the adhesive mass layer is more unlikely to be sticky.

Due to water contained in the adhesive mass fluid, the percutaneous permeability of the physiologically active substance is improved, and the pharmacological action of the physiologically active substance is more effectively exerted.

It is preferable that the content of water is 10 to 90% by mass, more preferably 15 to 88% by mass, and even more preferably 18 to 85% by mass, based on the mass of the whole adhesive mass fluid.

It is preferable that the adhesive mass fluid comprises a methyl acrylate/2-ethylhexyl acrylate copolymer resin. When the weight of the adhesive mass layer in a conventional gel patch is small, the water content is likely to be low, and adhesion strength is likely to be poor. However, due to the methyl acrylate/2-ethylhexyl acrylate copolymer resin contained in the adhesive mass layer, there is a tendency that a sufficient adhesion strength is likely to be maintained even after a lapse of a long period of time even when the mass of the adhesive mass layer is relatively small.

It is preferable that the methyl acrylate/2-ethylhexyl acrylate copolymer resin is an aqueous emulsion in which water is used as a medium. It is also preferable that the methyl acrylate; 2-ethylhexyl acrylate copolymer resin emulsion is an emulsion in which polyoxyethylene nonyl phenyl ether is used as a surfactant or a protective colloid. Also, it is preferable that the amount of the evaporation residue (non-volatile component) resulting from heating at temperatures higher than the boiling point of the medium (e.g., at 105° C. for 3 hours) is 57 to 61%. An example of such an emulsion is Nikasol TS-620 (trade name, manufactured by Nippon Carbide Industries Co., Inc.). According to the Japanese Pharmaceutical Excipients (2013), the amount of evaporation residue is 57 to 61% when Nikasol TS-620 is evaporated to dryness on a water bath and then dried at 105° C. for 3 hours.

Other medicaments, solubilizers, crosslinking agents, moisturizing agents, cooling agents, stabilizers, inorganic powders, colorants, flavorings, pH adjusters, and the like may be added as further components to the adhesive mass fluid.

Moreover, the composition may contain fruit-derived components such as rose fruit extract, orange extract, orange juice, raspberry extract, kiwi extract, cucumber extract, *gardenia* extract, grapefruit extract, black thorn extract, Zanthoxylum fruit extract, hawthorn extract, common juniper extract, jujube extract, *Lansium domesticum* extract, tomato extract, grape extract, loofah extract, lime juice, apple extract, apple juice, lemon extract, and lemon juice, water-soluble placental extract, allantoin, lecithin, amino acids, kojic acid, protein, sugars, hormones, placental extract, extraction components from various galenicals such as aloe and licorice, *Angelica keiskei* extract, avocado extract, *Hydrangea macrophylla* extract, althea extract, *arnica* extract, ginkgo extract, fennel extract, turmeric extract, oolong tea extract, *Scutellaria baicalensis* extract, *Phellodendron amurense* extract, barley extract, watercress extract, seaweed extract, hydrolyzed elastin, hydrolyzed wheat powder, hydrolyzed silk, chamomile extract, *Artemisia capillaris* extract, licorice extract, karkade extract, guanosine, *Sasa veitchii* extract, walnut extract, *clematis* extract, yeast extract, burdock extract, comfrey extract, bilberry extract, Bupleurum extract, umbilical extract, *salvia* extract, *Saponaria officinalis* extract, bamboo extract, black thorn extract, shiitake mushroom extract, *Rehmannia glutinosa* extract, *Lithospermi radix* extract, basswood extract, meadowsweet extract, calamus root extract, birch extract, field horsetail extract, honeysuckle extract, *Hedera helix* extract, hawthorn extract, *Sambucus nigra* extract, yarrow extract, peppermint extract, common mallow extract, swertia herb extract, jujube extract, thyme extract, clove extract, cogon extract, chenpi extract, orange peel extract, *Houttuynia cordata* extract, fermented-soybean extract, *ginseng* extract, *Rosa canina* extract, hibiscus extract, *Ophiopogon japonicus* extract, parsely extract, honey, *parietaria* extract, *Plectranthus japonicus* extract, bisabolol, coltsfoot extract, butterbur extract, poria extract, butcher's broom extract, propolis, peppermint extract, linden extract, hop extract, pine extract, horse chestnut extract, Asian skunk cabbage extract, *Sapindus mukurossi* extract, peach leaf extract, *Centaurea cyanus* extract, *eucalyptus* extract, *Citrus junos* fruit extract, mugwort extract, lavender extract, lettuce extract, *Astragalus sinicus* extract, rose extract, rosemary extract, *Anthemis nobilis* extract, royal jelly extract, or the like.

The solubilizer is not particularly limited as long as it can dissolve the medicament, and examples include crotamiton; N-methylpyrrolidone; polyalkylene glycols such as polyethylene glycol (PEG) and polybutylene glycol; fatty acid esters such as isopropyl myristate and diethyl adipate; oxyalkylene fatty acid esters such as polyethylene glycol monostearate; fatty acid esters such as polyoxyalkylene sorbitan fatty acid esters; polyoxyethylene hydrogenated castor oil; and surfactants such as polysorbate 80. One of these solubilizers may be used singly, or two or more may be used in combination. It is preferable to regulate the content of the solubilizer to 0.1 to 10% by mass based on the mass of the whole adhesive mass layer.

The moisturizer is not particularly limited as long as it can suppress evaporation of water from the adhesive mass layer that is associated with the lapse of time. Examples of the moisturizer include sorbitol, ethylene glycol, propylene glycol, polyethylene glycol, liquid paraffin, and polyhydric alcohols such as 1,3-propanediol and 1,4-butanediol. One of these moisturizers may be used singly, or two or more may be used in combination. It is preferable to regulate the content of the moisturizer to 3 to 70% by mass based on the mass of the whole adhesive mass layer.

Examples of the cooling agent include thymol, 1-menthol, d1-menthol, 1-isopulegol, and mentha oil, and it is preferable to use 1-menthol. It is preferable to regulate the content of the cooling agent to 0.5 to 3% by mass based on the mass of the whole adhesive mass layer.

Examples of the stabilizer include oxybenzone, dibutylhydroxytoluene (BHT), sodium edetate, and UV absorbers (such as dibenzoylmethane derivatives). It is preferable to regulate the content of the stabilizer to 0.01 to 3% by mass based on the mass of the whole adhesive mass layer.

Crosslinking agents, inorganic powders, colorants, flavorings, and pH adjusters that are commonly used in gel patches can be used.

It is preferable that the viscosity of the adhesive mass fluid is 50 to 90 Pa·s (50000 to 90000 cP), and more preferably 52 to 85 Pa·s (52000 to 85000 cP). When the viscosity of the adhesive mass fluid is 50 Pa·s (50000 cP) or more, there is a tendency that the components of the adhesive mass fluid are unlikely to ooze out to the backing fabric when spreading the adhesive mass fluid onto the backing fabric, and when 90 Pa·s (90000 cP) or less, a sufficient flowability can be secured and, in this regard, it is easy to spread the adhesive mass fluid onto the backing fabric.

The viscosity of the adhesive mass fluid can be regulated by a person skilled in the art to a desired value by changing the content of the physiologically active substance, water-soluble polymer, glycerin, or water.

It is preferable that the storage modulus of the composition for forming the adhesive mass layer is 500 to 10000 Pa, and more preferably 600 to 9500 Pa, when spreading the composition onto the backing fabric. It is preferable that the loss modulus of the composition for forming the adhesive mass layer is 500 to 8500 Pa, and more preferably 600 to 8300 Pa, when spreading the composition onto the backing fabric. Also, from a different perspective, it is preferable that the loss tangent (tan δ) of the composition for forming the adhesive mass layer is 0.7 to 1.0, and more preferably 0.8 to 1.0, when spreading the composition onto the backing fabric. The above values are all values measured at a frequency of 1 Hz at 32° C.

In particular, when the elongation recovery ratio of the backing fabric is 80 to 98%, it is preferable that the loss tangent of the composition is 0.75 to 1.0, and more preferably 0.8 to 1.0. Also, when the bending resistance of the backing fabric is 10 to 18 mm, it is preferable that the loss tangent of the composition is 0.75 to 1.0, and more preferably 0.8 to 1.0. When the course direction/wale direction ratio of the 50% modulus of the backing fabric (the value of the 50% modulus in the wale direction relative to the 50% modulus in the course direction) is 0.8 to 1.2, it is preferable that the loss tangent of the composition is 0.75 to 1.0, and more preferably 0.8 to 1.0.

The tan δ value of the adhesive mass fluid can be regulated by a person skilled in the art to a desired value by changing the content of the physiologically active substance, water-soluble polymer, glycerin, or water. In order to regulate the tan δ value of the adhesive mass fluid, it is more effective to change the content of the water-soluble polymer. As will be described below, the tan δ value of the adhesive mass fluid tends to decrease as the time passes, and therefore the tan δ value of the adhesive mass fluid may be regulated, such that the tan δ value when spreading the adhesive mass fluid onto the backing fabric is a desired value, by regulating the time from preparing the adhesive mass fluid to spreading it onto the backing fabric. In this case, for example, when a certain period of time is necessary from preparing the adhesive mass fluid to spreading it onto the backing fabric, the content of water in the adhesive mass fluid may be increased in advance according to the situations of the gel patch production site.

The gel patch may be provided with a release liner. The release liner is laminated on the surface of the adhesive mass layer on the side opposite the backing fabric. When the release liner is provided, there is a tendency that a decrease of the water content of the adhesive mass layer can be suppressed, and attachment of foreign matter and the like to the adhesive mass layer can be reduced, during storage.

The material of the release liner is not particularly limited, and a liner commonly known to people skilled in the art can be used. Examples of the material of the release liner include polyethylene, polypropylene, polyethylene terephthalate, and paper. One may be used singly, or two or more may be used in combination.

The gel patch may be stored in a pouch. With the gel patch being stored in a pouch, a decrease of the water content of the adhesive mass layer can be suppressed, and attachment of foreign matter and the like to the adhesive mass layer can be reduced.

It is preferable that the mass of the adhesive mass layer is, for example, 300 g/m² or more, and more preferably 400 g/m² or more. Also, it is preferable that the mass of the adhesive mass layer is, for example, 750 g/m² or less. A particularly preferable mass of the adhesive mass layer is 400 to 450 g/m², and by regulating the mass to the above range, the adhesive mass layer fits well, and an improved adhesion can be maintained over a longer period of time. When the mass of the adhesive mass layer is within the above range, the overall thickness of the gel patch can be reduced, the gel patch is likely to conform to the skin, moreover, the level difference relative to the surrounding part is small when the gel patch is attached, and therefore there is a tendency that the gel patch is unlikely to peel off.

Examples

The present invention will now be described in more detail by way of Examples and Comparative Examples.

In the Examples, backing fabrics A, B, and C were used.

(1-1) Elongation-Recovery Test of Backing Fabric (1)

Moduli when backing fabrics A to C were stretched in the course direction or the wale direction relative to the mesh were measured. That is to say, moduli exerted on the backing fabrics were measured when the backing fabrics were stretched in the course direction or the wale direction only such a distance that a specific modulus was attained. As for the term "elongation", when described as a "measurement starting position", a backing fabric is meant that is in a completely unstretched state, and when described as a "10% modulus", a backing fabric is meant that is in a state of being stretched from the measurement starting position in the course direction or the wale direction so as to have a strain of 10%.

Results are shown in Table 1. Numbers in Table 1 mean measured values of stress (unit: N).

TABLE 1

| | Stretch | Measurement starting position | 10% Modulus | 20% Modulus | 30% Modulus |
|---|---|---|---|---|---|
| Backing fabric A | Elongation (Course direction) | 0.000 | 0.071 | 0.378 | 0.746 |
| | Recovery (Course direction) | 0.000 | 0.012 | 0.089 | 0.209 |
| | Elongation (Wale direction) | 0.000 | 0.126 | 0.423 | 0.834 |
| | Recovery (Wale direction) | 0.000 | 0.038 | 0.168 | 0.364 |
| Backing fabric B | Elongation (Course direction) | 0.000 | 0.080 | 0.393 | 0.777 |
| | Recovery (Course direction) | 0.000 | 0.023 | 0.146 | 0.318 |
| | Elongation (Wale direction) | 0.000 | 0.123 | 0.345 | 0.632 |
| | Recovery (Wale direction) | 0.000 | 0.063 | 0.195 | 0.376 |
| Backing fabric C | Elongation (Course direction) | 0.000 | 0.062 | 0.432 | 0.977 |
| | Recovery (Course direction) | 0.000 | 0.006 | 0.093 | 0.256 |
| | Elongation (Wale direction) | 0.000 | 0.220 | 0.898 | 1.975 |
| | Recovery (Wale direction) | 0.000 | 0.051 | 0.303 | 0.718 |

| | Stretch | Measurement starting position | 40% Modulus | 50% Modulus |
|---|---|---|---|---|
| Backing fabric A | Elongation (Course direction) | 0.000 | 1.106 | 1.456 |
| | Recovery (Course direction) | 0.000 | 0.418 | 1.465 |
| | Elongation (Wale direction) | 0.000 | 1.381 | 2.094 |

TABLE 1-continued

| | | | | |
|---|---|---|---|---|
| | Recovery (Wale direction) | 0.000 | 0.709 | 2.118 |
| Backing fabric B | Elongation (Course direction) | 0.000 | 1.160 | 1.544 |
| | Recovery (Course direction) | 0.000 | 0.570 | 1.554 |
| | Elongation (Wale direction) | 0.000 | 0.994 | 1.438 |
| | Recovery (Wale direction) | 0.000 | 0.649 | 1.453 |
| Backing fabric C | Elongation (Course direction) | 0.000 | 1.575 | 2.209 |
| | Recovery (Course direction) | 0.000 | 0.573 | 2.226 |
| | Elongation (Wale direction) | 0.000 | 3.481 | 5.580 |
| | Recovery (Wale direction) | 0.000 | 1.515 | 5.656 |

(1-2) Elongation-Recovery Test of Backing Fabric (2)

The elongation recovery ratio (%), the bending resistance (mm), and the 50% modulus (N/5 cm) when backing fabrics A, B, and C were stretched in the course direction or the wale direction relative to the mesh were measured. The elongation recovery ratio and the bending resistance were measured by the methods described in JIS L 1096:2010.

Results are shown in Table 2.

TABLE 2

| | | Backing fabric A | Backing fabric B | Backing fabric C |
|---|---|---|---|---|
| | Weight [g/sheet] | 1.14 | 1.55 | 2.13 |
| Elongation recovery ratio [%] | Course direction | 72.5 | 83.1 | 74.6 |
| | Wale direction | 81.2 | 87.5 | 84.2 |
| | Ratio of course direction/wale direction | 0.89 | 0.95 | 0.89 |
| Bending resistance [mm] | Course direction | 12.3 | 12.3 | 16.7 |
| | Wale direction | 15.3 | 16.3 | 20.7 |
| | Ratio of course direction/wale direction | 0.80 | 0.75 | 0.81 |
| 50% Modulus [N/5 cm] | Ratio of course direction/wale direction | 0.70 | 1.06 | 0.40 |

(2-1) Preparation of Adhesive Mass Fluid

The adhesive mass fluid of Example 1 was prepared according to the formulation provided in Table 3. Numbers in Table 3 mean part by mass, and others indicate components.

TABLE 3

| | Example 1 |
|---|---|
| Ketoprofen | 2.0 |
| Gelatin | 2.5 |
| Partially-neutralized polyacrylate | 5.0 |
| Nikasol TS-620 | 17.0 |
| Inorganic powder | 1.0 |
| Propylene glycol | 10.0 |
| Glycerin | 15.0 |
| Purified water | 42.0 |
| Other components | 5.5 |
| Total | 100 |

(2-2) Dynamic Viscoelasticity Test of Adhesive Mass Fluid

Using the adhesive mass fluid of Example 1 as a sample, the loss modulus and the storage modulus were measured under the following conditions to calculate the loss tangent (the tan δ value).

[Measurement Conditions]

Apparatus: Rotary rheometer (manufactured by Rheometric Scientific F.E., Ltd.)

Sample part: Parallel plates with 25 mm diameter

Gap distance: 7 mm

Sample amount: 2 to 3 g

Temperature: 32° C.

Frequency: 1 Hz

Strain: 1%

The results of calculating the loss tangent (the tan δ value) from the storage modulus and loss modulus values obtained by the dynamic viscoelasticity test are provided in Table 4. The "time" in Table 4 means the time elapsed from preparing the adhesive mass fluid to performing the dynamic viscoelasticity test. As the time passed, the loss tangent (the tan δ value) of the adhesive mass fluid of Example 1 gradually decreased. After the lapse of each period of time, the adhesive mass fluid was spread onto the backing fabric, and it was possible to uniformly apply the adhesive mass fluid when the tan δ value was 0.75 or more.

TABLE 4

| Elapsed Time | tan δ |
|---|---|
| 1.5 Hours | — |
| 2.5 Hours | 0.99 |
| 3.5 Hours | 0.92 |
| 4.5 Hours | 0.76 |
| 5.5 Hours | 0.7 |
| 2 Weeks | 0.35 |

(2-3) Preparation of Adhesive Mass Fluid

The adhesive mass fluids of Examples 2 to 4 and Comparative Examples 1 to 2 were prepared according to the formulations provided in Table 5. Numbers in Table 5 mean part by mass.

TABLE 5

| | Comparative Example 1 | Example 2 | Example 3 |
|---|---|---|---|
| Ketoprofen | 2.0 | 2.0 | 2.0 |
| Gelatin | 2.5 | 2.5 | 2.5 |
| Partially-neutralized polyacrylate | 2.0 | 3.0 | 4.0 |
| Nikasol TS-620 | 17.0 | 17.0 | 17.0 |
| Inorganic powder | 1.0 | 1.0 | 1.0 |
| Propylene glycol | 10.0 | 10.0 | 10.0 |
| Glycerin | 15.0 | 15.0 | 15.0 |
| Purified water | 45.0 | 44.0 | 43.0 |
| Other components | 5.5 | 5.5 | 5.5 |
| Total | 100 | 100 | 100 |

| | Example 4 | Comparative Example 2 |
|---|---|---|
| Ketoprofen | 2.0 | 2.0 |
| Gelatin | 2.5 | 2.5 |
| Partially-neutralized polyacrylate | 6.0 | 8.0 |
| Nikasol TS-620 | 17.0 | 17.0 |
| Inorganic powder | 1.0 | 1.0 |
| Propylene glycol | 10.0 | 10.0 |
| Glycerin | 15.0 | 15.0 |
| Purified water | 41.0 | 39.0 |
| Other components | 5.5 | 5.5 |
| Total | 100 | 100 |

(2-4) Viscosity Test and Dynamic Viscoelasticity Test of Adhesive Mass Fluid

Viscosity measurement and dynamic viscoelasticity measurement were performed on the resulting adhesive mass fluids of Examples 2 to 4 and Comparative Examples 1 to 2. Viscosity measurement was performed immediately after preparing the adhesive mass fluids, and dynamic viscoelasticity measurement was performed 2.5 hours and 1 month after preparing the adhesive mass fluids. Results are shown in Table 6. An increased content of the partially-neutralized polyacrylate resulted in a higher adhesive mass fluid viscosity, and a decreased tan δ value in dynamic viscoelasticity measurement.

TABLE 6

|  | Comparative Example 1 | Example 2 | Example 3 |
|---|---|---|---|
| Viscosity of adhesive mass fluid (Pa · s) | 30 | 52 | 60 |
| tan δ 2.5 Hours after preparation of adhesive mass fluid | 1.26 | 1.01 | 0.92 |
| 1 Month after preparation of adhesive mass fluid | 0.70 | 0.43 | 0.44 |

|  | Example 4 | Comparative Example 2 |
|---|---|---|
| Viscosity of adhesive mass fluid (Pa · s) | 85 | 120 |
| tan δ 2.5 Hours after preparation of adhesive mass fluid | 0.75 | 0.62 |
| 1 Month after preparation of adhesive mass fluid | 0.50 | 0.32 |

(3-1) Preparation of Gel Patch

The adhesive mass fluid of Example 1 or Comparative Example 1 was spread onto each of backing fabrics B and C to prepare gel patches.

(3-2) Ooze-Out Test.

The backing fabrics of the resulting gel patches were evaluated according to whether the fluid adhered to the examiner's finger and tackiness was felt when the surface on the side opposite the surface in contact with the adhesive mass layer was touched by the finger. As for the evaluation results, "X" was given when tackiness was felt, and "O" was given when no tackiness was felt.

Results are shown in Table 7. Oozing was observed when the adhesive mass fluid of Comparative Example 1 was used, whereas no oozing was observed when the adhesive mass fluid of Example 1 was used.

TABLE 7

|  | Backing fabric B | Backing fabric C |
|---|---|---|
| Example 1 | ○ | ○ |
| Comparative Example 1 | X | X |

(3-3) Adhesion Test

The adhesive mass fluid of Example 1 or Comparative Example 2 was spread onto each of backing fabrics A to C to prepare gel patches. One of each resulting gel patch was affixed to the skin of the right and left elbow and lumbar regions of 15 subjects, and the peeling of the gel patches 8 hours and 24 hours after being affixed was visually evaluated. Evaluations were made according to the evaluation criteria provided in Table 8 based on the proportion of the area of the gel patch separated from the skin 8 hours and 24 hours after being affixed relative to the area of the gel patch brought into contact with the skin when the gel patch was affixed.

TABLE 8

| Peeling after 8 hours | Peeling after 24 hours | Evaluation |
|---|---|---|
| 0% or more and less than 20% | 0% or more and less than 20% | ○ |
|  | 20% or more and less than 50% | Δ |
|  | 50% or more and 100% or less | X |
| 20% or more and less than 50% | 20% or more and less than 50% | Δ |
|  | 50% or more and 100% or less | X |
| 50% or more and 100% or less | 50% or more and 100% or less | X |

Results are shown in Table 9. The gel patch prepared from the adhesive mass fluid of Example 1 exhibited excellent adhesion strength even 24 hours after attachment. On the other hand, the adhesive mass fluid of Comparative Example 2 had a high viscosity, and it was not possible to uniformly spread it onto the backing fabrics.

TABLE 9

|  | Backing fabric A | Backing fabric B | Backing fabric C |
|---|---|---|---|
| Example 1 | ○ | ○ | Δ |
| Comparative Example 2 | — | — | — |

Concerning the adhesive mass fluids of Examples 2 to 4 and Comparative Examples 1 to 2 as well, the gel patches were prepared using backing fabrics A, B, and C, and the oozing test and the adhesion test were performed.

Results are shown in Table 10. When the adhesive mass fluid of Comparative Example 1 was used, oozing to the back side of the backing fabrics was observed when the adhesive mass fluid was spread, and the adhesive mass fluid was difficult to uniformly spread onto the backing fabrics. On the other hand, when the adhesive mass fluid of Comparative Example 2 was used, no oozing to the back side of the backing fabrics was observed, but the adhesive mass fluid had a high viscosity, and it was not possible to uniformly spread it. In contrast, when the adhesive mass fluids of Examples 2 to 4 were used, it was possible to uniformly spread them onto the backing fabrics, oozing was suppressed, and, moreover, the results of the adhesion test were also good.

TABLE 10

|  | Comparative Example 1 | Example 2 | Example 3 | Example 4 | Comparative Example 2 |
|---|---|---|---|---|---|
| Oozing test | X | ○ | ○ | ○ | ○ |
| Adhesion test | — | ○ | ○ | ○ | — |

Also, the adhesive mass fluids of Examples 5 to 40 were prepared in which felbinac, diclofenac sodium, methyl salicylate, glycol salicylate, indomethacin, loxopro fen sodium, diphenhydramine, lidocaine, or fentanyl was used in place of ketoprofen of Examples 1 to 4 (Examples 5 to 8 are where felbinac was used in place of ketoprofen of Examples 1 to 4, and Examples 9 to 40 correspond to the physiologically active substances in the described order.) to produce gel patches. The oozing test and the adhesion test were performed on the resulting gel patches, and each of the obtained gel patch showed good results.

Furthermore, adhesive mass fluids containing agar, glucomannan, pectin, or carrageenan in place of gelatin in the formulations of Examples 1 to 4 (Examples 41 to 44 are where agar was used in place of gelatin of Examples 1 to 4, and Examples 45 to 56 correspond to the water-soluble polymers in the described order) were prepared to produce respective gel patches. The oozing test and the adhesion test were performed on the resulting gel patches, and all gel patches showed good results.

The invention claimed is:

1. A method for producing a gel patch comprising an adhesive mass layer on a backing fabric, comprising:
   a step of preparing a composition comprising a physiologically active substance, a water-soluble polymer comprising a polyacrylic acid or a neutralized polyacrylate, a methyl acrylate/2-ethylhexyl acrylate copolymer resin, glycerin, and water; and
   a step of applying the composition to the backing fabric to form the adhesive mass layer, wherein
   a loss tangent of the composition in dynamic viscoelasticity measurement at 1 Hz at the time of application to the backing fabric is 0.75 to 1, and the backing fabric is a knitted fabric;
   an elongation recovery ratio of the knitted fabric is 73 to 98% in a course direction and 83 to 98% in a wale direction;
   the knitted fabric has a ratio of a 50% modulus in a wale direction relative to a 50% modulus in a course direction of 0.8 to 1.2; and
   wherein the modulus is measured as defined in JIS L 1018:1999.

2. The method according to claim 1, wherein
   a bending resistance of the knitted fabric is 10 to 15 mm in a course direction and 10 to 18 mm in a wale direction.

3. The method according to claim 2, wherein a content of the water-soluble polymer is 3 to 18% by mass based on the mass of the whole adhesive mass layer.

4. The method according claim 1, wherein a content of the water-soluble polymer is 3 to 18% by mass based on the mass of the whole adhesive mass layer.

5. A gel patch, which is obtained by e method according to claim 1.

* * * * *

UNITED STATES PATENT AND TRADEMARK OFFICE
CERTIFICATE OF CORRECTION

PATENT NO.        : 10,940,121 B2
APPLICATION NO.   : 15/551916
DATED             : March 9, 2021
INVENTOR(S)       : Seiichiro Tsuru and Masayoshi Maki Page 1 of 1

It is certified that error appears in the above-identified patent and that said Letters Patent is hereby corrected as shown below:

In the Claims

Claim 5, Column 16, Line 19, please delete the phrase "obtained by e method" and replace with "obtained by the method".

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*